(12) United States Patent
Kim et al.

(10) Patent No.: US 10,067,138 B2
(45) Date of Patent: Sep. 4, 2018

(54) FLUORESCENT PARTICLE COMPRISING GOLD NANOPARTICLES AND METHOD FOR MANUFACTURING SAME

(71) Applicant: Medisensor, Inc., Daegu (KR)

(72) Inventors: So yeon Kim, Daegu (KR); Nae Young Heo, Daegu (KR); Jeaan Jung, Daegu (KR); Won Jung Kim, Daegu (KR); Byung Gap Hwang, Daegu (KR); Young Seop Kim, Daegu (KR); Myoung Hoon Lee, Goyang-si (KR)

(73) Assignee: MEDISENSOR, INC., Daegu (KR)

( * ) Notice: Subject to any disclaimer, the term of this patent is extended or adjusted under 35 U.S.C. 154(b) by 262 days.

(21) Appl. No.: 14/913,801

(22) PCT Filed: Aug. 18, 2014

(86) PCT No.: PCT/KR2014/007639
§ 371 (c)(1),
(2) Date: Mar. 31, 2016

(87) PCT Pub. No.: WO2015/026117
PCT Pub. Date: Feb. 26, 2015

(65) Prior Publication Data
US 2016/0356781 A1 Dec. 8, 2016

(30) Foreign Application Priority Data

Aug. 23, 2013 (KR) .................. 10-2013-0100430
Aug. 5, 2014 (KR) .................. 10-2014-0100689

(51) Int. Cl.
*C09K 11/87* (2006.01)
*C09K 11/02* (2006.01)
(Continued)

(52) U.S. Cl.
CPC .......... *G01N 33/587* (2013.01); *C09K 11/025* (2013.01); *C09K 11/06* (2013.01);
(Continued)

(58) Field of Classification Search
CPC ....... C09K 11/87; C09K 11/025; C09K 11/06; C09K 11/58; C09K 11/7734;
(Continued)

(56) References Cited

U.S. PATENT DOCUMENTS

| 4,587,223 A | 5/1986 | Soini et al. |
| 8,956,553 B2 | 2/2015 | Zhou et al. |

(Continued)

FOREIGN PATENT DOCUMENTS

| KR | 20120089928 A | 8/2012 |
| WO | WO-2013076305 A1 | 5/2013 |

OTHER PUBLICATIONS

Ma et al., "A microemulsion preparation of nanoparticles of europium in silica with luminescence enhancement using silver", Feb. 3, 2009, IOPScience Nanotechnology 20, pp. 1-7. (Year: 2009).*

(Continued)

*Primary Examiner* — Matthew E. Hoban
*Assistant Examiner* — Lynne Edmondson
(74) *Attorney, Agent, or Firm* — Lucas & Mercanti, LLP (57) ABSTRACT

Provided are a fluorescent particle and a method for manufacturing the same. The fluorescent particle may include a gold nanoparticle; a silica shell covering the gold nanoparticle; and lanthanide group complex particles dispersed in the silica shell. Each of the lanthanide group complex particles may include a lanthanide group ion; a ligand bonded to the lanthanide group ion and including phosphorus; and a ligand bonded to the lanthanide group ion and having a beta diketone functional group. The fluorescent particle is observable with the naked eye and may emit light (Continued)

when ultraviolet light is irradiated. The fluorescent particle may be used for detecting and analyzing biomaterial samples.

9 Claims, 4 Drawing Sheets (51) Int. Cl.
*C09K 11/06* (2006.01)
*C09K 11/58* (2006.01)
*G01N 33/58* (2006.01)

(52) U.S. Cl.
CPC .......... *C09K 11/58* (2013.01); *G01N 33/582* (2013.01); *G01N 33/585* (2013.01); *C09K 2211/1011* (2013.01); *C09K 2211/1044* (2013.01); *C09K 2211/1092* (2013.01); *C09K 2211/182* (2013.01); *G01N 2458/40* (2013.01)

(58) Field of Classification Search
CPC ............ C09K 11/873; C09K 2211/185; C09K 2211/182; G01N 2458/40; G01N 33/587

USPC ..................................... 252/301.4 F, 301.4 R
See application file for complete search history.

(56) References Cited

U.S. PATENT DOCUMENTS

2004/0067503 A1* 4/2004 Tan .................. B82Y 15/00
435/6.1
2011/0097723 A1* 4/2011 Liu .................. B82Y 15/00
435/6.1

OTHER PUBLICATIONS

Zhi Ya Ma et al. "A microemulsion preparation of nanoparticles of europium in silica with luminescence enhancement using silver". IOP Science. Nanotechnology 20. 2009. pp. 1-7.
International Search Report PCT/ISA/210 for International Application No. PCT/KR2014/007639 dated Dec. 9, 2014.

* cited by examiner

FLUORESCENT PARTICLE COMPRISING GOLD NANOPARTICLES AND METHOD FOR MANUFACTURING SAME

TECHNICAL FIELD

The present invention disclosed herein relates to a fluorescent particle, and more particularly, to a fluorescent particle including a gold nanoparticle and lanthanide group complex particles.

BACKGROUND ART

A fluorescent particle including metal such as gold or silver has a fluorescent characteristic improved due to a surface plasmon resonance phenomenon. The fluorescent particle may improve detection sensitivity of target molecules, and thus may be used to detect DNA and/or RNA, perform biological analysis including immunity, and sense molecules. Further, the fluorescent particle may be used in a measurement device and a chemical device. As described above, the fluorescent particle is extensively used in molecular biology, material science, photonics, and medical science.

A reverse microemulsion method is used during a process for applying organic nanoparticles on a silica. In the reverse microemulsion method, an organic nanoparticle size and a particle distribution may be simply controlled. For example, a research result was reported, in which fullerene-silica nanoparticles were manufactured in a size of tens nanometers by the reverse microemulsion method. In this case, fullerene and silica are directly connected by a covalent bond without a separate linker.

Recently, biotechnologies and technologies of many various studies have been blended and developed while affecting various fields. Among them, many technologies have been developed with regard to biomaterial analysis and detection markets. One of methods used to analyze and measure a biomaterial is a technology using nanoparticles or beads, in which measurement is performed while the biomaterial is attached to a side of a microparticle or a nanoparticle.

Fluorescence occurs when electrons are emitted by electron transference while a material in an excited state returns to the material in a bottom state by absorbing photons by molecules. A fluorescent material absorbs energy having a predetermined wavelength to emit energy having another wavelength. The fluorescent material includes an inorganic material and an organic material to be used as a fluorescent dye or pigment, such as fluorescent ink and fluorescent paint, or the like.

DISCLOSURE OF THE INVENTION

Technical Problem

The present invention provides a fluorescent particle that may be applied to measure a biomaterial.

The present invention also provides a fluorescent particle that is observable with the naked eye and may be detected when ultraviolet light is irradiated.

Technical Solution

Embodiments of the present invention provide fluorescent particles and methods for manufacturing the same. The fluorescent particle includes a gold nanoparticle; a silica shell covering the gold nanoparticle; and lanthanide group complex particles dispersed in the silica shell, in which each of the lanthanide group complex particles may include a lanthanide group ion; a ligand bonded to the lanthanide group ion and including phosphorus; and a ligand bonded to the lanthanide group ion and having a beta diketone functional group.

In some embodiments, a surface of the silica shell may have a hydrophilic functional group.

In other embodiments, the ligand including phosphorus may include at least one selected from trioctylphosphine oxide and trioctylphosphine, and the beta diketone ligand may include at least one selected from 4,4,4-trifluoro-1-(2-naphthyl)-1,3-butanedione, 4,4,4-trifluoro-1-(2-thienyl)-1, 3-butanedione, 1,3-diphenyl-1,3-propanedione, and benzil.

In still other embodiments, the lanthanide group complex particles may further include at least one selected from 1,10-phenanthroline monohydrate and 2,2'-bipyridyl.

In even other embodiments, the lanthanide group ion may include an europium ion, a dysprosium ion, a samarium (Sm) ion, or a terbium ion.

In other embodiments of the present invention, methods for manufacturing a fluorescent particle include preparing a gold nanoparticle and lanthanide group complex particles; manufacturing a silica by hydrolysis and condensation reactions of a silicon precursor; and manufacturing a silica shell surrounding the gold nanoparticle by adding the gold nanoparticle and the lanthanide group complex to the silica, in which the lanthanide group complex particles may be formed in the silica shell due to agglomeration of the lanthanide group complexes, and each of the lanthanide group complex particles may include a lanthanide group ion; a ligand bonded to the lanthanide group ion and including phosphorus; and a ligand bonded to the lanthanide group ion and having a beta diketone functional group.

In some embodiments, the preparing of the gold nanoparticle may include adding a surfactant to a gold precursor solution; and reducing the gold precursor solution.

In other embodiments, the ligand including phosphorus may include at least one selected from trioctylphosphine oxide and trioctylphosphine, and the beta diketone ligand may include at least one selected from 4,4,4-trifluoro-1-(2-naphthyl)-1,3-butanedione, 4,4,4-trifluoro-1-(2-thienyl)-1, 3-butanedione, 1,3-diphenyl-1,3-propanedione, and benzil.

In still other embodiments, the manufacturing of the silica and the manufacturing of the silica shell may be performed by using a surfactant.

Advantageous Effects

A fluorescent particle may include a gold nanoparticle, lanthanide group complex particles, and a silica shell. Since the gold nanoparticle, the lanthanide group complex particles, and the silica shell do not have toxicity, the fluorescent particle may be suitable for analysis/detection of bio-samples/biomaterials.

The gold nanoparticle may emit light in a visible ray region by a surface plasmon phenomenon to easily distinguish whether a fluorescent particle-biosample conjugate is generated or not with the naked eye. A size of the gold nanoparticle may be adjusted to control a wavelength of light in a visible ray region, which is emitted from the gold nanoparticle.

The lanthanide group complex particles may have a fluorescent characteristic that light having a wavelength in a ultraviolet light region is absorbed to emit light having a wavelength in a visible ray region. The fluorescent particle may emit light when ultraviolet light is irradiated. A kind and a number of ligands of the lanthanide group complex particles may be adjusted to control the wavelength and the intensity of light emitted from the lanthanide group complex particles. The lanthanide group complex particles may be plurally provided in the silica shell. Since the fluorescent characteristic of the fluorescent particle is improved by the lanthanide group complex particles, the fluorescent particle may be used to analyze biosamples/biomaterials in a small amount.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

MODE FOR CARRYING OUT THE INVENTION

Hereinafter, preferred embodiments of the present invention will be described in detail with reference to the accompanying drawings. Advantages and features of the present invention, and methods achieving them will be apparent by embodiments as will be described later, together with the accompanying drawings. However, the present invention may not be limited to the embodiments set forth herein, but be embodied in different forms. Rather, the embodiments presented herein are provided to make this disclosure to be thorough and complete, and to fully convey the spirit of the present invention to those skilled in the art, and the present invention will only be defined by the scope of the claims. Like reference numerals denote like elements throughout the specification.

The terms used in the present specification are set forth to illustrate the embodiments but are not to be construed to limit the present invention. In the present specification, a singular form may include a plural from as long as it is not specifically mentioned in a sentence. Terms "comprises" and/or "comprising" used in the specification represent that one or more components, steps, operations, and/or elements exist or are added. Further, reference numerals suggested according to the order of description are based on the preferred embodiments, and thus are not limited to the order of description. In addition, in the present specification, it will be understood that when a layer is referred to as being on another layer or substrate, it can be the layer directly formed on another layer or substrate or an intervening layer may also be present.

Furthermore, the embodiments disclosed in the present specification will be described with reference to the idealistic illustrative cross-sectional views and/or plane views of the present invention. In the drawings, component thicknesses and/or sizes may be exaggerated for effective description of the technical contents. As such, variations from the shapes of the illustrations as a result, for example, of manufacturing techniques and/or tolerances, are to be expected. Thus, embodiments should not be construed as limited to the particular shapes of regions illustrated herein but may include deviations in shapes that result, for example, from manufacturing. For example, an etched region shown to have a right angle may have a round shape or a shape having a predetermined curvature. Accordingly, regions illustrated in the drawings have rough properties, and also have shapes which are set forth to illustrate a particular form of regions of devices but not to limit the scope of the invention.

Hereinafter, a fluorescent particle according to a concept of the present invention will be described with reference to the accompanying drawings.

Figure 1:
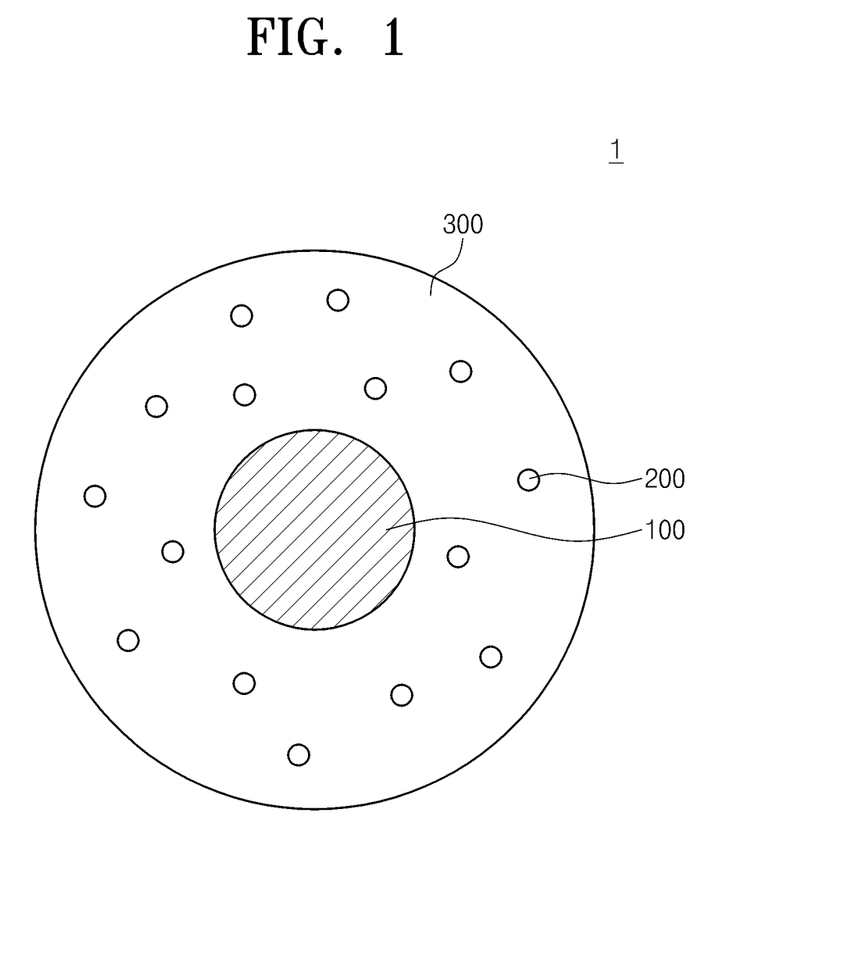
FIG. 1 shows a fluorescent particle according to an embodiment.

FIG. 1 shows a fluorescent particle according to an embodiment.

Referring to FIG. 1, a fluorescent particle 1 may include a gold nanoparticle 100, lanthanide group complex particles 200, and a silica shell 300. The fluorescent particle 1 may have a core-shell structure. The fluorescent particle 1 may be bonded to a biosample/biomaterial to form a fluorescent particle-biosample conjugate. The fluorescent particle 1 may be used to detect and analyze the biosample/biomaterial.

The gold nanoparticle 100 may be provided to a core of the fluorescent particle 1. The gold nanoparticle 100 may have a sphere shape. The gold nanoparticle 100 may emit light in a visible ray region by a surface plasmon resonance phenomenon. Accordingly, the gold nanoparticle 100 may exhibit a color. The gold nanoparticle 100 may have a size of about 10 nm to about 60 nm.

Figure 2:
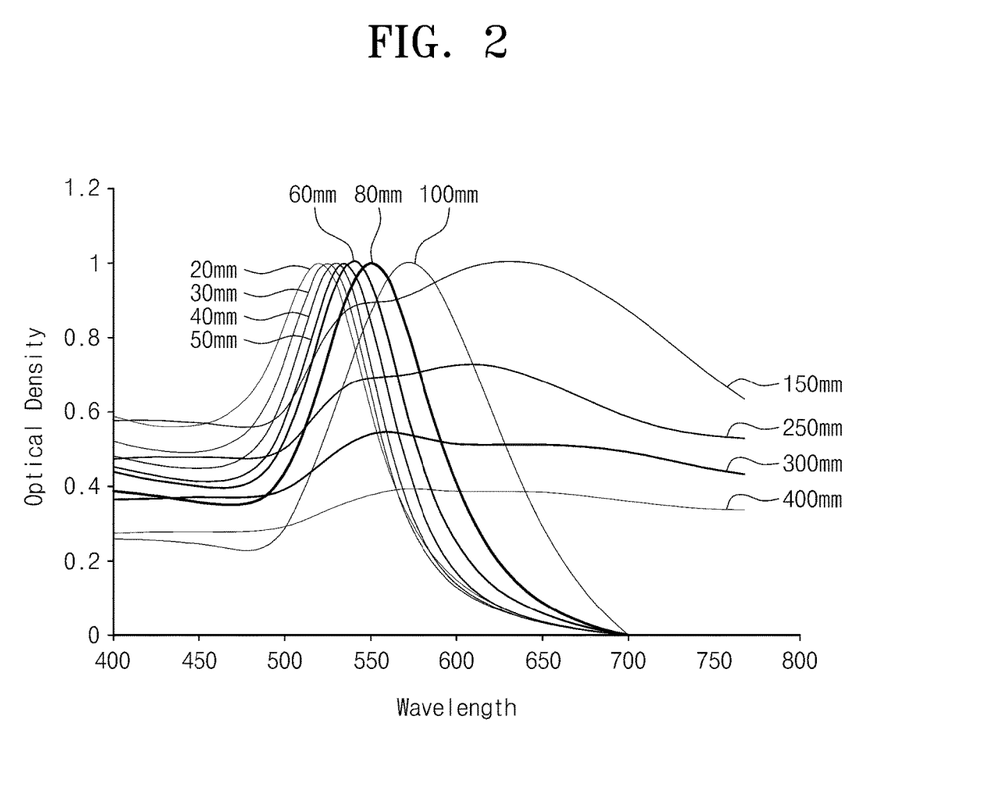
FIG. 2 is a graph showing an optical density according to a wavelength, which is shown according to a size of a gold nanoparticle.

Referring to FIG. 2 together with FIG. 1, as the size of the gold nanoparticle 100 is increased, the wavelength of emitted light in the visible ray region may be increased. The size of the gold nanoparticle 100 may be adjusted to control the wavelength of light in the visible ray region emitted from the gold nanoparticle 100. For example, during a manufacturing process of the gold nanoparticle 100, a surfactant may be used to adjust the size of the gold nanoparticle 100. As another example, when the gold nanoparticle 100 is manufactured, a reaction condition such as a temperature, a reaction time, a reducing agent, and/or a kind of solvent may be controlled to control the size of the gold nanoparticle 100. In the case where the fluorescent particle 1 is used to detect and analyze the biosample such as a diagnostic kit, by light in the visible ray region emitted from the gold nanoparticle 100, it may be easily distinguished whether the fluorescent particle 1-biosample conjugate is formed or not with the naked eye. The gold nanoparticle 100 does not have toxicity and thus may be suitable to analyze the biosample/biomaterial.

Referring back to FIG. 1, the silica shell 300 may be provided to surround the gold nanoparticle 100 and cover the gold nanoparticle 100. The shell may include the silica. The silica shell 300 may include a hydrophobic functional group and a hydrophilic functional group. The gold nanoparticle 100 has hydrophobicity, and thus the hydrophobic functional group of the silica shell 300 may interact with the gold nanoparticle 100. Accordingly, the hydrophobic functional group of the silica shell 300 may be provided toward the gold nanoparticle 100, and the hydrophilic functional group may be provided toward the outside. For example, the hydrophilic functional group may include a hydroxyl group (—OH). Since the hydrophilic functional group of the silica shell 300 is disposed toward the outside, the fluorescent particle 1 may be easily dispersed in an aqueous solution including the biosample/biomaterial. As another example, in the fluorescent particle 1, through a reaction in the aqueous solution, various functional groups (for example, a carboxy group (COOH), an amine group ($NH_2$), a thiol group, an aldehyde group, and/or an epoxy group or the like) may be introduced into the surface of the silica shell 300. For example, the hydroxyl group on the surface of the silica shell 300 may be substituted by various functional groups. The functional group may be directly bonded to the biosample/biomaterial, or may be bonded to the biosample/biomaterial through the other molecule/material. Further, the silica shell 300 does not have toxicity, and thus may be suitable to analyze the biosample/biomaterial.

The lanthanide group complex particles 200 may be provided to be dispersed in the silica shell 300. The lanthanide group complex particles 200 may be provided in plurality. The lanthanide group complex particles 200 may have a fluorescent characteristic that light having a first wavelength is absorbed to emit light having second wavelength which is different from the first wavelength. In this case, the first wavelength may be a wavelength in an ultraviolet light region, and second wavelength may be a wavelength in a visible ray region. For example, europium ions may absorb light having a wavelength of about 340 nm to 390 nm (for example, 361 nm) to emit light having a wavelength of 600 to 650 nm (for example, 615 nm). By the lanthanide group complex particles 200, the fluorescent particle 1 may be used to analyze the biosample/biomaterial in a small amount. By the silica shell 300, the fluorescent particle 1 may include a plurality of lanthanide group complex particles 200. As the amount of the lanthanide group complex particles 200 included in the fluorescent particle 1 is increased, the intensity of light having second wavelength emitted from the fluorescent particle 1 may be increased. Accordingly, when the fluorescent particle 1 is used in the biosample/biomaterial, the detection intensity may be improved.

Hereinafter, the lanthanide group complex particles of the present invention will be described in more detail.

Figure 3:
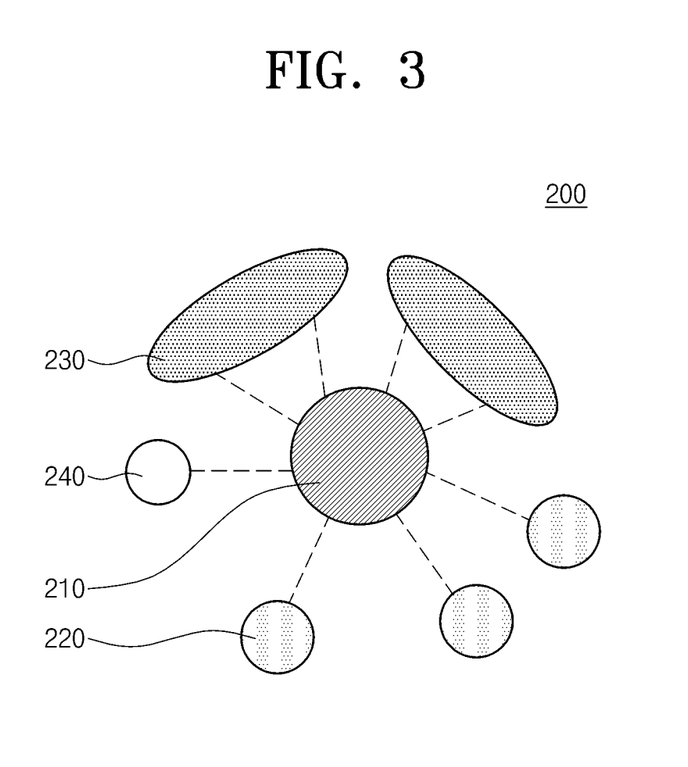
FIG. 3 shows a lanthanide group complex according to the embodiment.

FIG. 3 shows the lanthanide group complex particle according to the embodiment. The content that overlaps the aforementioned description will be omitted.

Referring to FIG. 3, the lanthanide group complex particle 200 may include a lanthanide group ion 210 and ligands 220, 230, and 240. Hereinafter, the lanthanide group ion 210 may serve as a central atom. In the case where the lanthanide group ion 210 includes a cadmium (Cd) ion, due to toxicity of the cadmium ion, the lanthanide group complex particle 200 may not be suitable for diagnosis, measurement, or detection of biomolecules. The lanthanide group complex particle 200 of the present invention includes the lanthanide group ion 210 having a nontoxic property, for example, an europium (Eu) ion, a dysprosium (Dy) ion, a samarium (Sm) ion, or a terbium (Tb) ion, and thus may be suitable for detection/analysis of the biosample/biomaterial. The lanthanide group ion 210, as described above, may have a fluorescent characteristic that light having a first wavelength is absorbed to emit light having second wavelength which is different from the first wavelength.

The ligands 220, 230, and 240 may be bonded to the lanthanide group ion 210. The lanthanide group complex particle 200 may include at least one the ligand 220 including phosphorus, and at least one beta diketone ligands 230. The lanthanide group complex particle 200 may further include the ligand 240 including nitrogen. The lanthanide group complex particle 200 may include the ligands 220, 230, and 240 to increase the intensity of fluorescence of the lanthanide group ion 210. The beta diketone ligand 230 may serve to transfer electrons during a process for embodying the fluorescent characteristic of the europium ion. An increase action of the intensity of fluorescence of the ligand 220 including phosphorus may be embodied when the ligand 220 and the beta diketone ligand 230 are included in the lanthanide group complex particle 200. The number of ligands 220 including phosphorus and beta diketone ligands 230 may be adjusted to adjust the intensity of emission and an emission wavelength of the lanthanide group complex particle 200. The ligand 230 including phosphorus may be, for example, trioctylphosphine oxide (hereinafter, TOPO) or trioctylphosphine (hereinafter, TOP). The beta diketone ligand 220 may include at least one selected from 4,4,4-trifluoro-1-(2-naphthyl)-1,3-butanedione (hereinafter, NTA), 4,4,4-trifluoro-1-(2-thienyl)-1,3-butanedione (hereinafter, TTA), 1,3-diphenyl-1,3-propanedione (hereinafter, DPP), and benzil. The ligand 240 including nitrogen may include at least one selected from 1,10-phenanthroline monohydrate (hereinafter, Phen) and 2,2'-bipyridyl (hereinafter, Bipy).

Table 1 shows the lanthanide group complex particles according to the examples of the present invention and Structural Formulas thereof.

TABLE 1

| Name | Structural Formula |
|---|---|
| Tris[4,4,4-trifluoro-1-(2-thienyl)-1,3-butanedionato]tris(trioctylphosphine oxide)europium(III) | (structure shown) |

R = (CH$_2$)$_2$CH$_2$

TABLE 1-continued

| Name | Structural Formula |
| --- | --- |
| Tris[4,4,4-trifluoro-1-(2-thienyl)-1,3-butanedionato]tris(trioctylphosphine)europium(III) | <br>R = (CH$_2$)$_2$CH$_2$ |
| Tris[4,4,4-trifluoro-1-(2-naphthyl)-1,3-butanedione]tris(trioctylphosphine oxide)europium(III) | <br>R = (CH$_2$)$_2$CH$_2$ |
| Tris[4,4,4-trifluoro-1-(2-naphthyl)-1,3-butanedione]tris(trioctylphosphine oxide)europium(III) | <br>R = (CH$_2$)$_2$CH$_2$ |

TABLE 1-continued

| Name | Structural Formula |
|---|---|
| Tris(1,3-diphenyl-1,3-propanedione)tris(trioctylphosphine oxide)europium(III) | (structure shown) R = $(CH_2)_2CH_3$ |
| Tris(1,3-diphenyl-1,3 propanedione)tris(trioctylphosphine)europium(III) | (structure shown) R = $(CH_2)_2CH_3$ |
| 1,3-diphenyl-1,3-propanedione tris[4,4,4-trifluoro-1-(2-thienyl)-1,3-butanedionato]tris(trioctylphosphine oxide europium(III) | (structure shown) R = $(CH_2)_2CH_3$ |

TABLE 1-continued

| Name | Structural Formula |
|---|---|
| 1,3-diphenyl-1,3-propanedione tris[4,4,4-trifluoro-1-(2-thienyl)-1,3-butanedionato]trioctylphosphine europium(III) | R = (CH₂)₂CH₂ |
| 1,3-diphenyl-1,3-propanedione di[4,4,4-trifluoro-1-(2-thienyl)-1,3-butanedionato]tri(trioctylphosphine oxide)europium(III) | R = (CH₂)₂CH₂ |
| 1,3-diphenyl-1,3-propanedione di[4,4,4-trifluoro-1-(2-thienyl)-1,3-butanedionato]tri(trioctylphosphine)europium(III) | R = (CH₂)₂CH₂ |

TABLE 1-continued

| Name | Structural Formula |
| --- | --- |
| Di(1,3-diphenyl-1,3-propanedione)[4,4,4-trifluoro-1-(2-thienyl)-1,3-butanedionato]tri(trioctylphosphine oxide)europium(III) | <br>R = (CH$_2$)$_2$CH$_2$ |
| Di(1,3-diphenyl-1,3-propanedione)[4,4,4-trifluoro-1-(2-thienyl)-1,3-butanedionato]tri(trioctylphosphine)europium(III) | <br>R = (CH$_2$)$_2$CH$_2$ |
| 1,3-diphenyl-1,3-propanedione 2,2'-Bipyridyl trioctylphosphine europium(III) | <br>R = (CH$_2$)$_2$CH$_2$ |

TABLE 1-continued

| Name | Structural Formula |
|---|---|
| Dibenzil[4,4,4-trifluoro-1-(2-thienyl)-1,3-butanedionato]tri(trioctylphosphine)europium(III) | (structure shown) |

R = (CH₂)₂CH₂

Hereinafter, a method for manufacturing a fluorescent particle according to the embodiment will be described with reference to the accompanying drawings.

Figure 4:
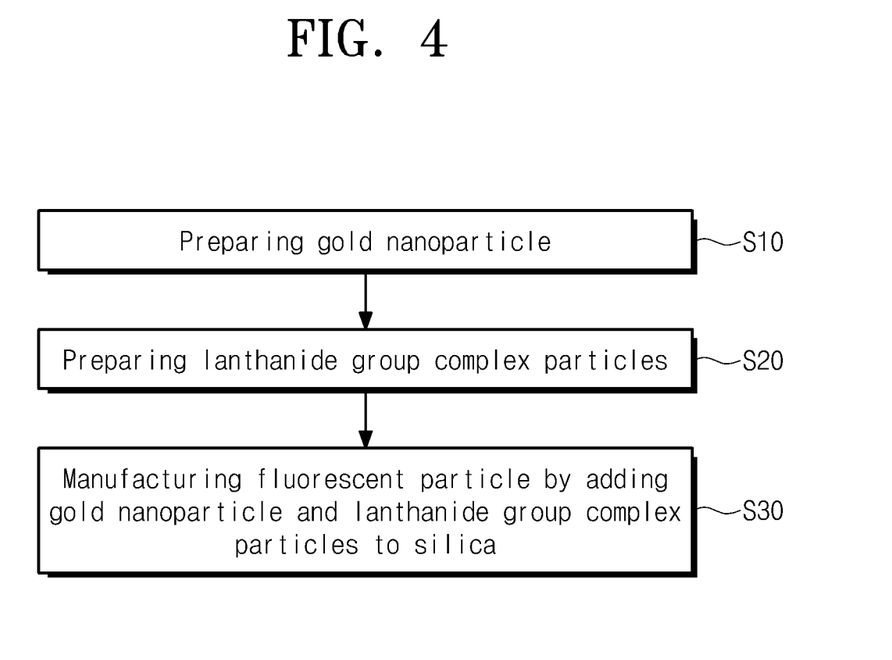
FIG. 4 is a flowchart showing a method for manufacturing the fluorescent particle according to the embodiment of the present invention.

FIG. 4 is a flowchart showing the method for manufacturing the fluorescent particle according to the embodiment of the present invention. Hereinafter, the content that overlaps the aforementioned description will be omitted.

Referring to FIG. 4 together with FIG. 1, a precursor solution of the gold nanoparticle may be reduced to prepare the gold nanoparticle 100 at step S10. A gold precursor and a first surfactant may be added to and mixed with a solvent to manufacture the gold precursor solution. A reduction reaction of the gold precursor solution may be performed under a temperature condition of about 110° C. for 5 hours. For example, the precursor solution of the gold nanoparticle 100 may be chloroauric acid. The first surfactant may be oleyl amine, but is not limited thereto and may be various. A kind of the first surfactant may be adjusted to control the size of the manufactured gold nanoparticle 100. As another example, a reducing agent may be further added, but a separate reducing agent may not be added by controlling a process condition. Subsequently, a washing process may be performed. The washing process may be performed three times by using ethanol. The manufactured gold nanoparticle 100 may be kept in an organic solvent such as cyclohexane.

Referring to FIG. 4 together with FIG. 3, the lanthanide group complex particle 200 may be prepared at step S20. For example, a lanthanide group element (for example, europium, dysprosium, samarium, or terbium), a ligand, a surfactant, and water may be mixed to manufacture a reaction solution. A kind of the ligand may be the same as those described in the examples of the ligands 220, 230, and 240 of FIG. 3. The kind and the ratio of the added ligand may be adjusted to control kinds and ratios of the ligands 220, 240, and 240 bonded to the lanthanide group ion 210. If the color of the reaction solution is a transparent white color, acrylic acid may be mixed with the reaction solution to complete manufacturing of the lanthanide group complex particle 200.

A silica may be manufactured by a condensation reaction of a silica precursor material. As an example, the silica may be manufactured according to the following Reaction Equation 1.

For example, tetraethyl orthosilicate (TEOS) may be used as the precursor material (a). The precursor material (a) may be dissolved in an organic solvent such as cyclohexane. The precursor material may be hydrolyzed to manufacture the silica precursor (b). The silica precursor (b) may be subjected to a condensation reaction under ammonium hydroxide to form the silica (c). In this case, a second surfactant may be further added to the silica. As an example, the second surfactant may be Igepal CO-520 (Sigma-Aldrich Co., LLC., polyoxyethylene (5) nonylphenylether), but is not limited thereto and may be various. A kind and an addition amount of the second surfactant may be controlled to adjust the size of the silica shell 300.

Referring to FIG. 4 together with FIG. 1, the gold nanoparticle 100 and the lanthanide group complex particles 200 may be added to the silica at step S30. Addition of the gold nanoparticle 100 and the lanthanide group complex particles 200 may be performed before the silica is manufactured. The gold nanoparticle 100, the lanthanide group complex particles 200, and the silica may be mixed for about 24 hours. The surface of the gold nanoparticle 100 has hydrophobicity, and thus the hydrophobic functional group of the silica may be disposed toward the gold nanoparticle 100. The silica may surround the gold nanoparticle 100 to form the silica shell 300. The gold nanoparticle 100 may correspond to a core. The lanthanide group complex particles 200 may be dispersed in the silica shell 300. The lanthanide group complex particles 200 may interact with the silica shell 300 to be stabilized. Accordingly, the intensity of fluorescence emitted from the lanthanide group complex particles 200 may be increased. The gold nanoparticle 100 and the lanthanide group complex particles 200 may be more easily carried in the silica shell 300 by the second surfactant. Accordingly, manufacturing of the fluorescent particle 1 shown in the example of FIG. 1 may be completed.

While this invention has been described in connection with what is presently considered to be practical exemplary embodiments with reference to the accompanying drawings, it is to be understood by those skilled in the art that the invention is not limited to the disclosed embodiments, but, on the contrary, is intended to cover various modifications and equivalent arrangements included within the spirit and scope of the appended claims.

The invention claimed is:

1. A fluorescent particle comprising:
a gold nanoparticle;
a silica shell covering the gold nanoparticle; and
lanthanide group complex particles dispersed in the silica shell,
wherein each of the lanthanide group complex particles includes
a lanthanide group ion;
a ligand bonded to the lanthanide group ion and including phosphorus; and
a ligand bonded to the lanthanide group ion and having a beta diketone functional group.

2. The fluorescent particle of claim 1, wherein a surface of the silica shell has a hydrophilic functional group.

3. The fluorescent particle of claim 1, wherein the ligand including phosphorus includes at least one selected from trioctylphosphine oxide and trioctylphosphine, and the beta diketone ligand includes at least one selected from 4,4,4-trifluoro-1-(2-naphthyl)-1,3-butanedione, 4,4,4-trifiuoro-1-(2-thienyl)-1,3-butanedione, 1,3-diphenyl- 1,3-propanedione, and benzil.

4. The fluorescent particle of claim 1, wherein the lanthanide group complex particles further include at least one selected from 1,10-phenanthroline monohydrate and 2,2'-bipyridyl.

5. The fluorescent particle of claim 1, wherein the lanthanide group ion includes an europium ion, a dysprosium ion, a samarium (Sm) ion, or a terbium ion.

6. A method for manufacturing a fluorescent particle, the method comprising:
preparing a gold nanoparticle and lanthanide group complex particles;
manufacturing a silica by hydrolysis and condensation reactions of a silicon precursor; and
manufacturing a silica shell surrounding the gold nanoparticle by adding the gold nanoparticle and the lanthanide group complex particles to the silica,
wherein the silica shell is fanned from the silica, the lanthanide group complex particles are provided while being dispersed in the silica shell, and
each of the lanthanide group complex particles includes
a lanthanide group ion;
a ligand bonded to the lanthanide group ion and including phosphoruss; and
a ligand bonded to the lanthanide group ion and having a beta diketone functional group.

7. The method of claim 6, wherein the preparing of the gold nanoparticle includes adding a surfactant to a gold precursor solution; and reducing the gold precursor solution.

8. The method of claim 6, wherein the ligand including phosphorus includes at least one selected from trioctylphosphine oxide and trioctylphosphine, and the beta diketone ligand includes at least one selected from 4,4,4-trifiuoro-1-(2-naphthyl)-1,3-butanedione, 4,4,4-trifiuoro- 1-(2-thienyl)-1,3-butanedione, 1,3-diphenyl- 1,3-propanedione, and benzil.

9. The method of claim 6, wherein the manufacturing of the silica and the manufacturing of the silica shell are performed by using a surfactant.

* * * * *